(12) United States Patent
Coulthard

(10) Patent No.: US 10,286,129 B2
(45) Date of Patent: May 14, 2019

(54) REDUCED-PRESSURE SYSTEMS, DRESSINGS, AND METHODS FACILITATING SEPARATION OF ELECTRONIC AND CLINICAL COMPONENT PARTS

(71) Applicant: KCI Licensing, Inc., San Antonio, TX (US)

(72) Inventor: Richard Daniel John Coulthard, Dorset (GB)

(73) Assignee: KCI Licensing, Inc., San Antonio, TX (US)

( * ) Notice: Subject to any disclaimer, the term of this patent is extended or adjusted under 35 U.S.C. 154(b) by 1192 days.

(21) Appl. No.: 14/386,444

(22) PCT Filed: Mar. 28, 2013

(86) PCT No.: PCT/US2013/034472
§ 371 (c)(1),
(2) Date: Sep. 19, 2014

(87) PCT Pub. No.: WO2013/149078
PCT Pub. Date: Oct. 3, 2013

(65) Prior Publication Data
US 2015/0057625 A1 Feb. 26, 2015

Related U.S. Application Data

(60) Provisional application No. 61/616,901, filed on Mar. 28, 2012.

(51) Int. Cl.
*A61M 1/00* (2006.01)
*A61F 13/00* (2006.01)
(Continued)

(52) U.S. Cl.
CPC ....... *A61M 1/009* (2014.02); *A61F 13/00068* (2013.01); *A61F 13/0206* (2013.01);
(Continued)

(58) Field of Classification Search
CPC .. A61M 1/009; A61M 1/0092; A61M 1/0094; A61M 1/0088; Y10T 29/49822;
(Continued)

(56) References Cited

U.S. PATENT DOCUMENTS

| | | |
|---|---|---|
| 1,355,846 A | 10/1920 | Rannells |
| 2,547,758 A | 4/1951 | Keeling |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

AU Application No. 2013237989 Examination Report dated Oct. 19, 2016.
(Continued)

*Primary Examiner* — Andrew J Mensh

(57) ABSTRACT

Systems, dressings, and related methods, for providing reduced pressure to a tissue site on a patient are presented that involve using a self-contained reduced-pressure dressing. The dressing includes an absorbent pouch and an electronics pouch. The absorbent pouch has an absorbent for absorbing liquid from the tissue site, and the electronics pouch has a pump for applying reduced pressure to the tissue site through the absorbent pouch. The electronics pouch is removably coupled to the absorbent pouch such that the electronics pouch and absorbent pouch may be easily separated for disposal.

25 Claims, 11 Drawing Sheets

(51) Int. Cl.
*A61F 13/02* (2006.01)
*B65D 75/30* (2006.01)

(52) U.S. Cl.
CPC ....... *A61F 13/0216* (2013.01); *A61M 1/0092* (2014.02); *A61M 1/0094* (2014.02); *B65D 75/30* (2013.01); *A61M 1/0088* (2013.01); *Y10T 29/49822* (2015.01)

(58) Field of Classification Search
CPC .. B65D 75/30; A61F 13/0068; A61F 13/0206; A61F 13/0216
USPC ........................................................ 604/319
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,910,125 A * | 6/1999 | Cummings ......... A61F 13/0246 128/888 |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 8,764,732 B2* | 7/2014 | Hartwell ........... A61F 13/00068 604/317 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0079852 A1 | 4/2006 | Bubb et al. |
| 2009/0227969 A1* | 9/2009 | Jaeb .................... A61M 1/0088 604/313 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| JP | 2011513003 A | 4/2011 |
| JP | 2012051640 A | 3/2012 |
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |

(56) References Cited

FOREIGN PATENT DOCUMENTS

| | | |
|---|---|---|
| WO | 96/05873 A1 | 2/1996 |
| WO | 97/18007 A1 | 5/1997 |
| WO | 99/13793 A1 | 3/1999 |
| WO | 2009111657 A2 | 9/2009 |
| WO | 2012057881 A1 | 5/2012 |

OTHER PUBLICATIONS

JP Application No. 2015503614 Notice of Rejection dated Feb. 14, 2017.
N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, the Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).
Examination Report for corresponding European Application No. 13716656.7 dated Jun. 17, 2016.

* cited by examiner

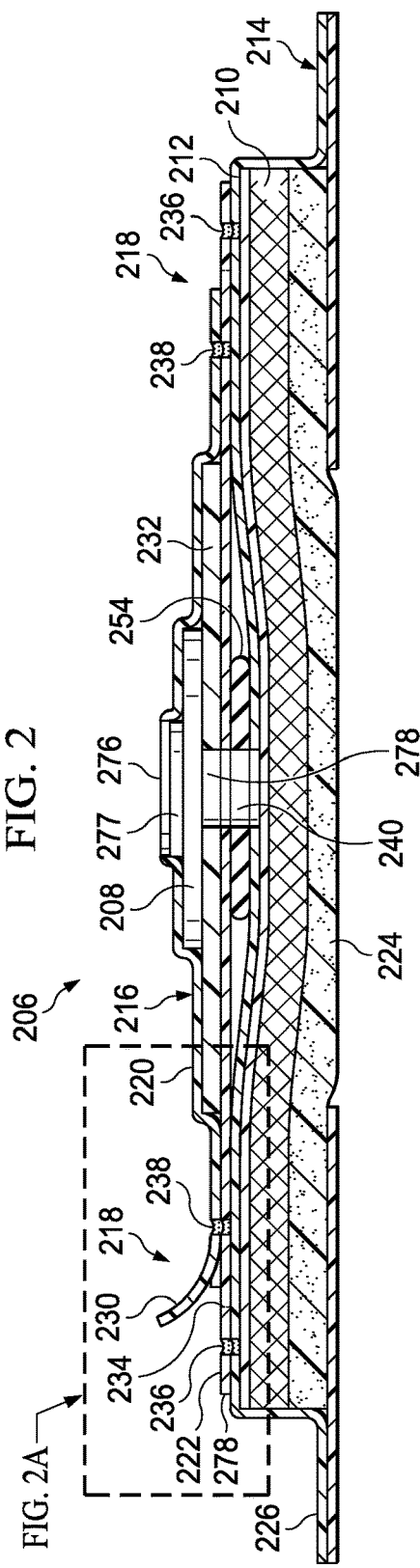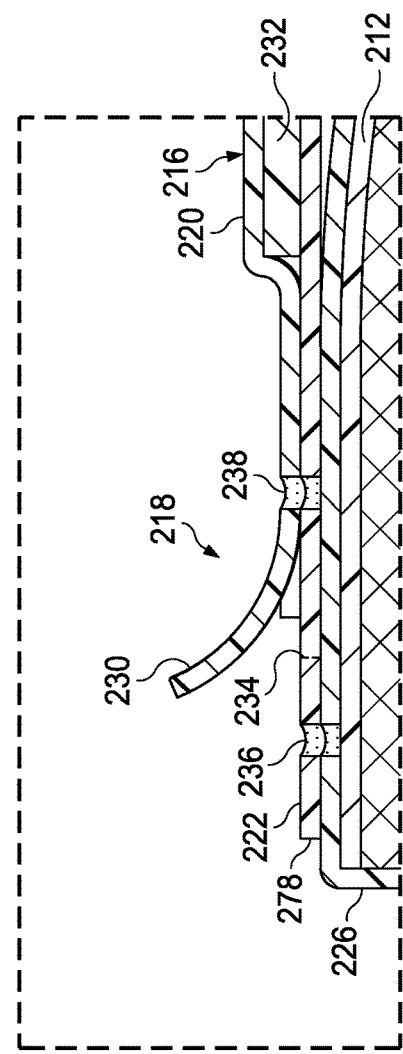

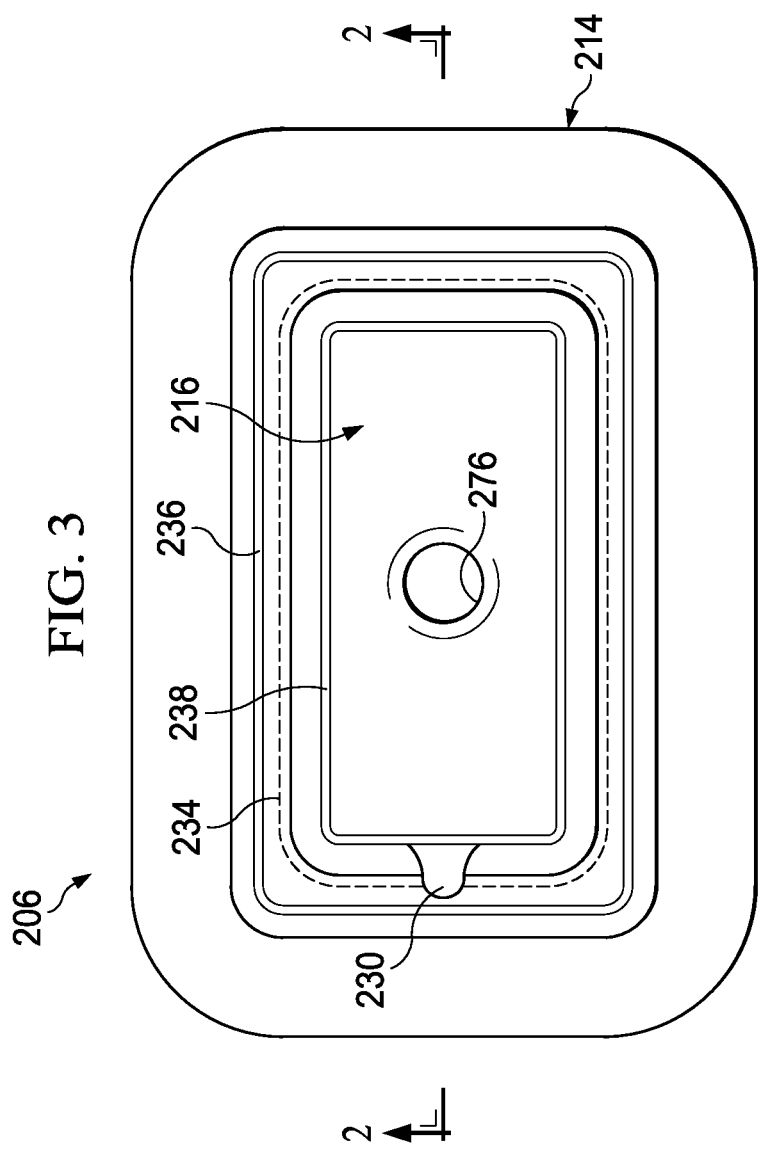

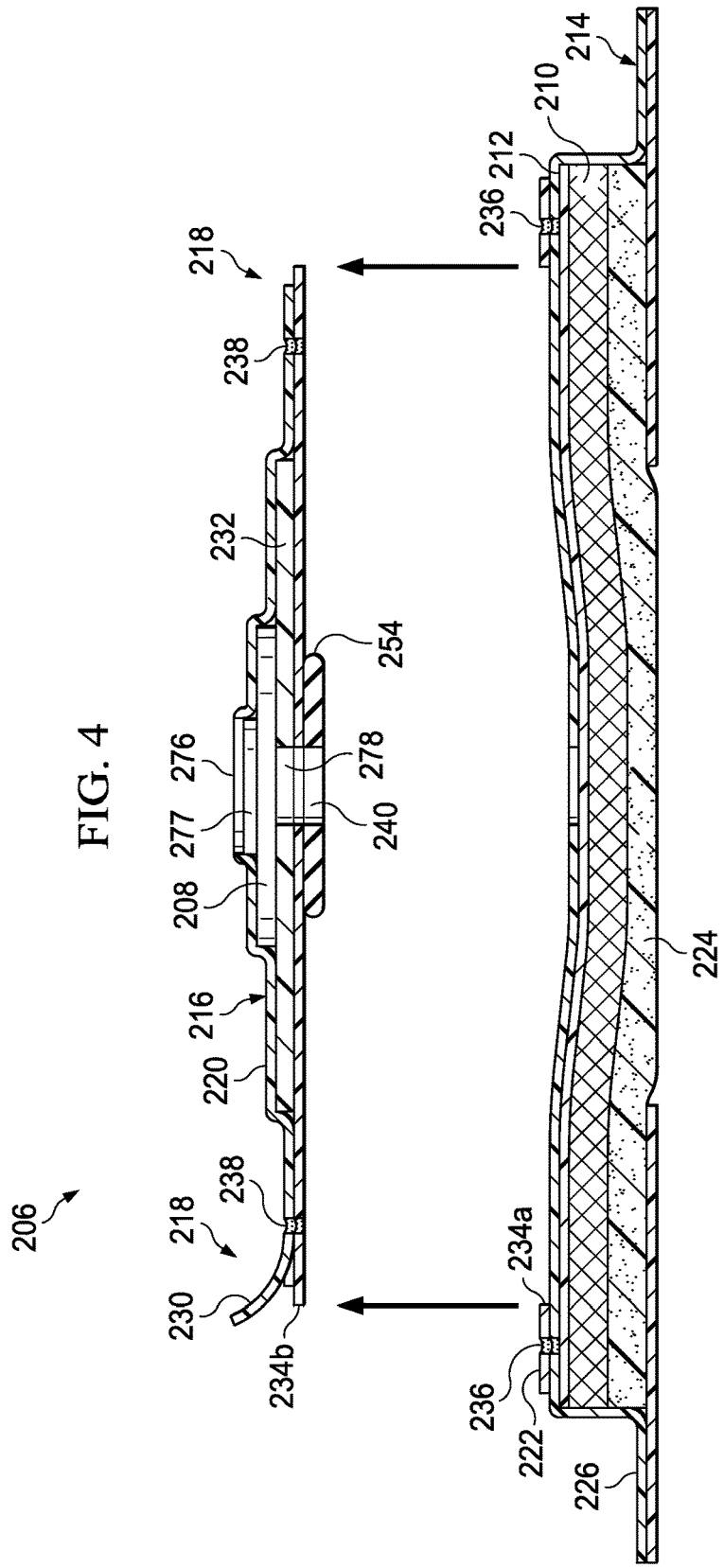

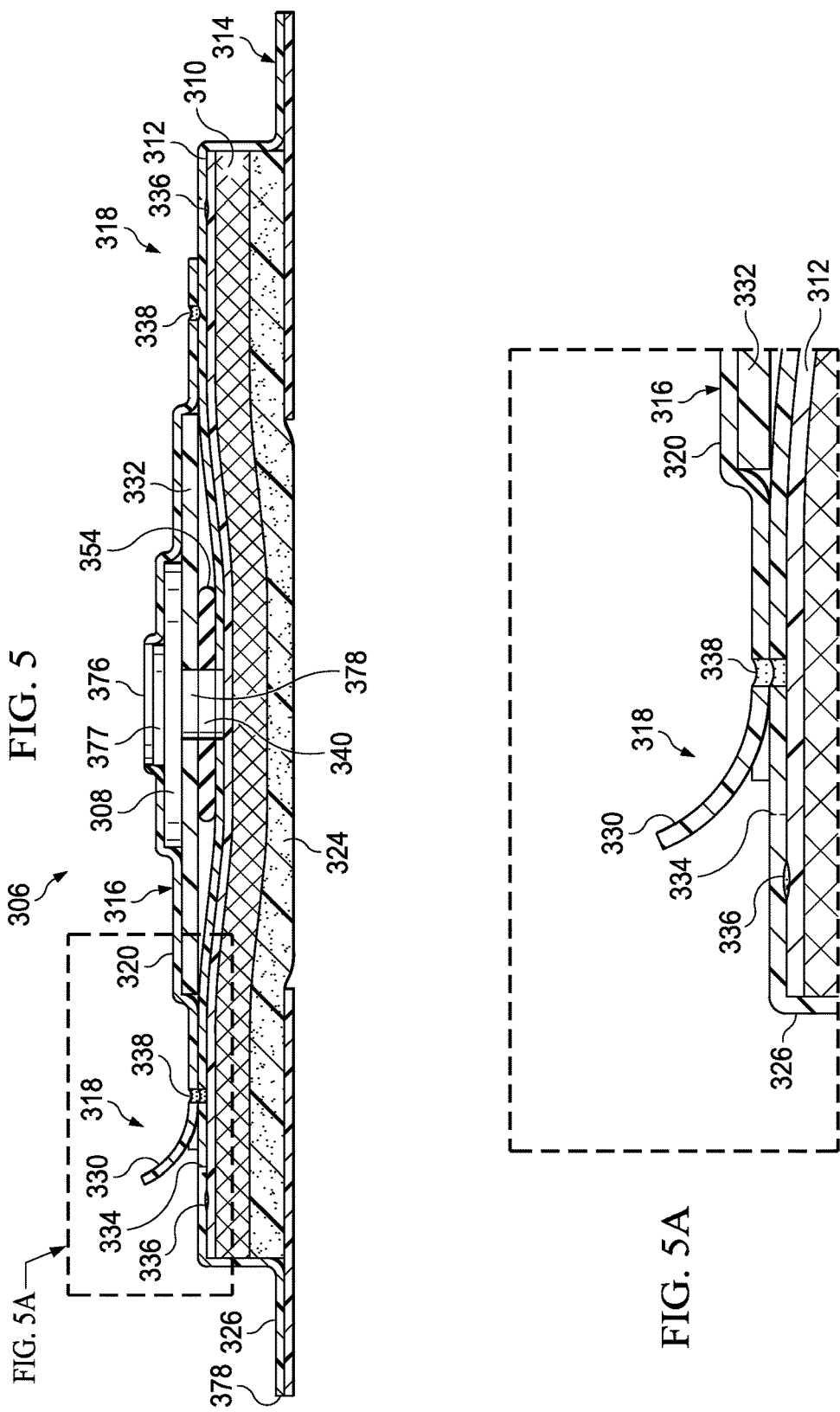

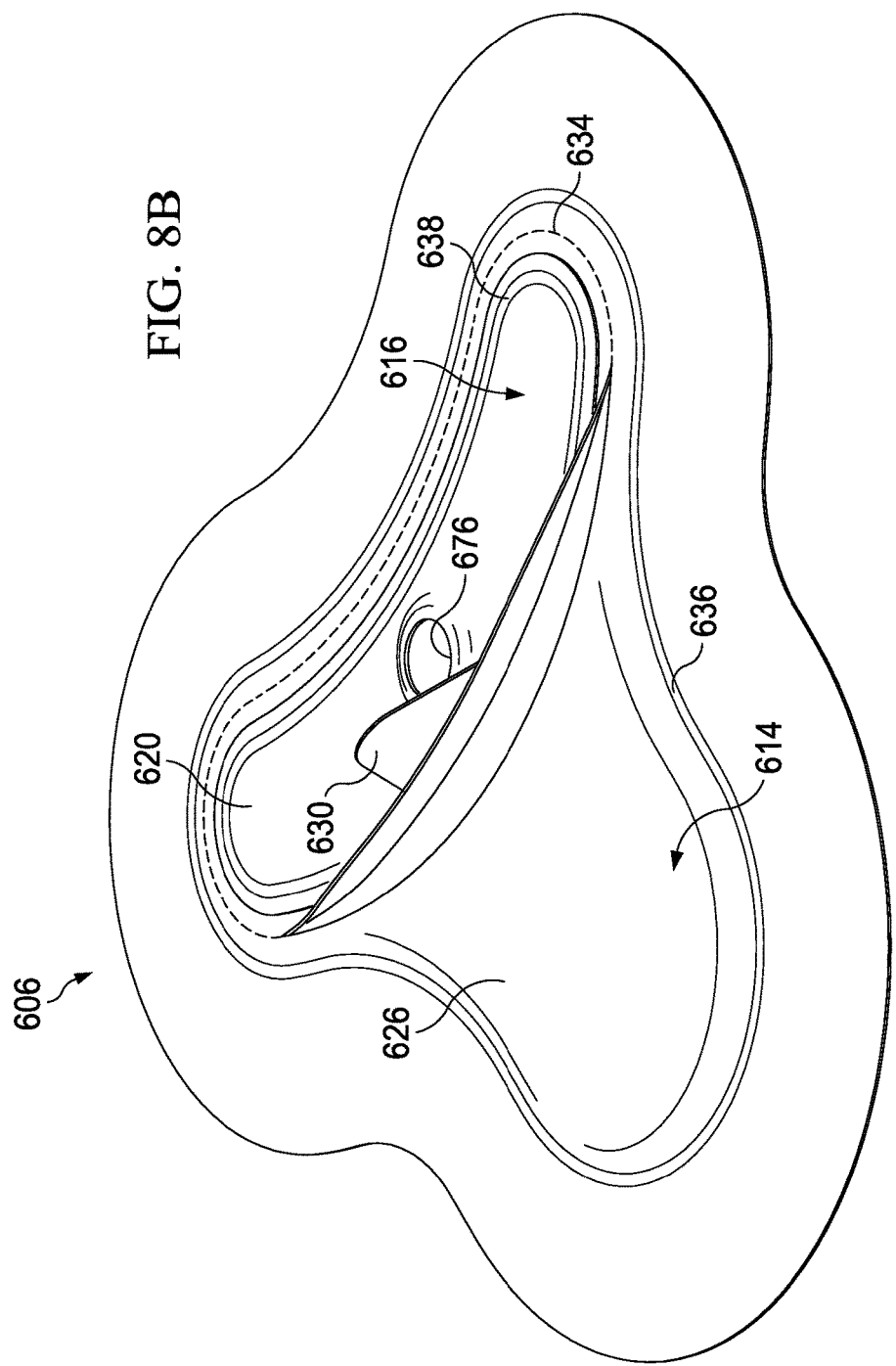

REDUCED-PRESSURE SYSTEMS, DRESSINGS, AND METHODS FACILITATING SEPARATION OF ELECTRONIC AND CLINICAL COMPONENT PARTS

REFERENCE TO RELATED APPLICATIONS

This application claims the benefit of U.S. provisional application No. 61/616,901, filed Mar. 28, 2012 and is herein incorporated by reference in its entirety.

FIELD

The present disclosure relates generally to medical treatment systems and, more particularly, but not by way of limitation, to reduced-pressure wound dressings, systems, and methods that facilitate the separation of clinical waste and electronics waste for efficient disposal.

BACKGROUND

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, when applied to open wounds, reduced pressure is applied to tissue through a porous pad or other manifold device of a reduced-pressure wound dressing. The porous pad distributes reduced pressure to the tissue and channels fluids that are drawn from the tissue into the dressing. When the reduced pressure therapy is completed or the reduced-pressure wound dressing is spent, the reduced-pressure wound dressing is removed from the tissue site and discarded.

SUMMARY

According to an illustrative embodiment, a reduced-pressure dressing for applying reduced pressure treatment to a tissue site includes an absorbent pouch and an electronics pouch. The absorbent pouch includes a manifold, an absorbent layer, and a first cover. The manifold layer is adapted to deliver reduced pressure to the tissue site, the absorbent layer is in fluid communication with the manifold layer to absorb liquid from at least one of the manifold layer and the tissue site, and the first cover is positioned over the absorbent layer and the manifold layer to maintain the reduced pressure at the tissue site. The electronics pouch is removably coupled to the absorbent pouch, and includes a pump and a second cover. The pump is adapted to provide fluid communication to the tissue site through at least one of the absorbent layer and the manifold layer, and the second cover has a first electronics cover and a second electronics cover. The second electronics cover is coupled to the first electronics cover and the pump is positioned between the first electronics cover and the second electronics cover.

Another illustrative embodiment includes a method for disposing of a reduced-pressure dressing. The reduced-pressure dressing includes an electronics pouch removably coupled to an absorbent pouch. The absorbent pouch includes a tissue manifold layer, an absorbent layer in fluid communication with the tissue manifold layer, and a first cover. The method comprises pulling the electronics pouch to separate electronics pouch from the absorbent pouch along a weakened coupling between the electronics pouch and the absorbent pouch.

According to another illustrative embodiment, a reduced-pressure dressing for applying reduced pressure treatment to a tissue site includes an absorbent pouch and a pump pouch. The absorbent pouch has an absorbent for absorbing liquid from the tissue site, and the pump pouch has a pump for applying reduced pressure to the tissue site through the absorbent pouch. The pump pouch is removably coupled to the absorbent pouch.

According to another illustrative embodiment, a reduced-pressure dressing for applying reduced pressure treatment to a tissue site includes a manifold layer and an absorbent layer. The manifold layer is adapted to be positioned at the tissue site and the absorbent layer is in fluid communication with the manifold layer. The reduced-pressure dressing includes a cover positioned over the absorbent layer to create a sealed space beneath the cover, and the cover has an aperture to allow fluid communication with the sealed space. The reduced-pressure dressing also includes an envelope comprising an upper sheet coupled to a lower sheet, and a pump positioned between upper and lower sheets. The reduced-pressure dressing includes a removable coupling between the envelope and the cover.

Other features and advantages of the illustrative embodiments will become apparent with reference to the drawings and detailed description that follow.

BRIEF DESCRIPTION OF THE DRAWINGS

FIG. 2 is a side, cross-section view of the illustrative reduced-pressure dressing of FIG. 1, including a removable coupling between an electronics pouch and an absorbent pouch of the reduced-pressure dressing;

FIG. 2A is a detail view of a portion of the reduced-pressure dressing that includes a perforation;

FIG. 3 is a top view of the reduced-pressure dressing;

FIG. 4 is a side, cross-section view of the reduced-pressure dressing that shows the electronics pouch being separated from the absorbent pouch;

FIG. 5 is a side, cross-section view showing another illustrative reduced-pressure dressing having a removable coupling between the electronics pouch and absorbent pouch of the reduced-pressure dressing;

FIG. 8B is a perspective view showing the electronics pouch of the reduced-pressure dressing of FIG. 8A being separated from the absorbent pouch along a perforation.

DETAILED DESCRIPTION OF ILLUSTRATIVE EMBODIMENTS

Figure 1:
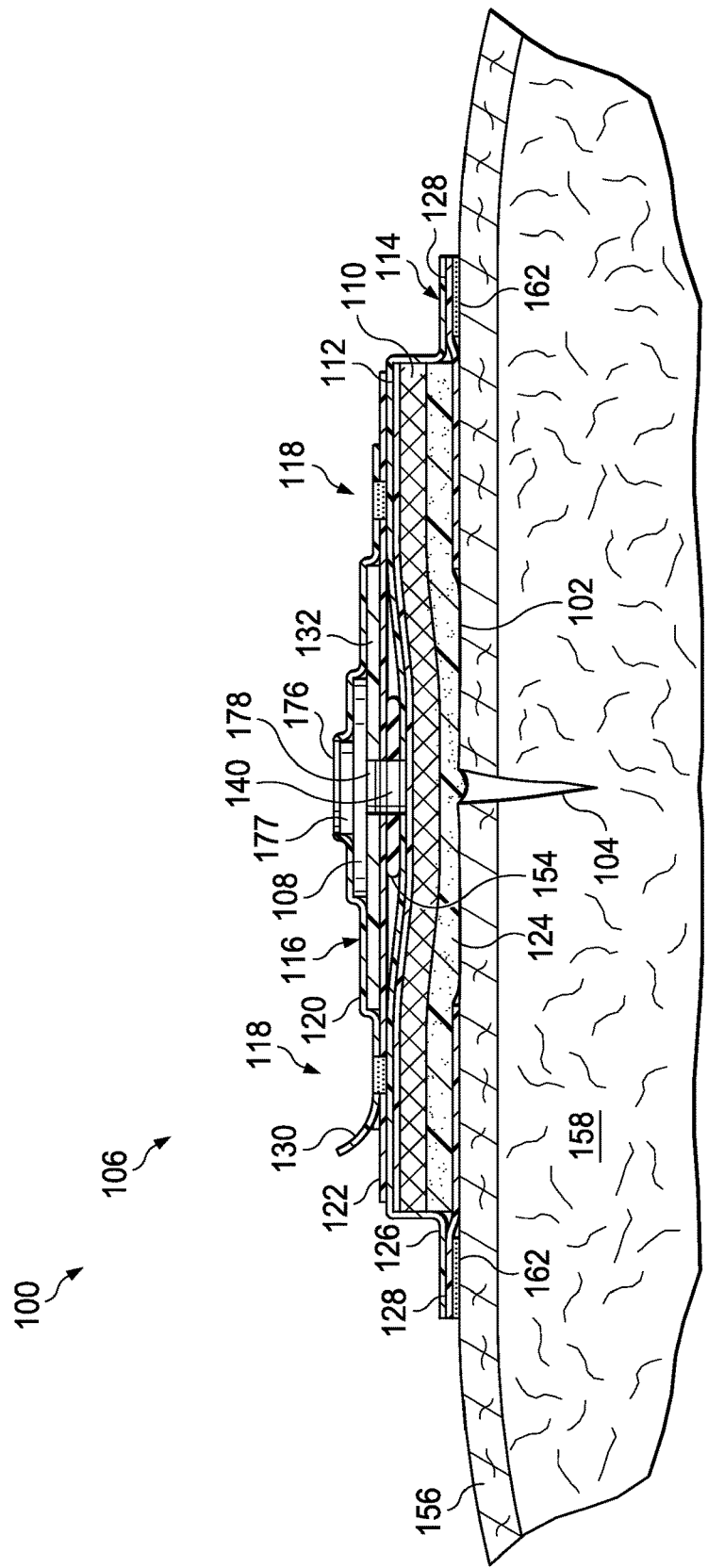
FIG. 1 is a side, cross-section view of an illustrative embodiment of a system for treating a tissue site with reduced pressure, including a reduced-pressure dressing coupled to the tissue site.

In the following detailed description of the illustrative, non-limiting embodiments, reference is made to the accompanying drawings that form a part hereof. In the accompanying drawings similar elements may have similar reference characters that are indexed to multiples of 100. These illustrative embodiments are described in sufficient detail to enable those skilled in the art to practice the invention. It is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments is defined only by the appended claims.

Wound dressings composed of traditional dressing materials typically do not contain electronic components. Yet recent and more advanced wound dressings include electronic components to deliver therapy to wounds and to monitor conditions at wound sites. This may pose a difficulty when the dressing has been used and the time comes to dispose of the dressing. Used wound dressings that include biological or clinical waste are frequently required by law to be disposed by approved methods. For example, regulations may require the incineration of clinical waste to limit the risk of spreading disease. Similarly, the disposal of electronic components is also regulated by law in many jurisdictions. Such regulations may require that used electronic components be disassembled and recycled, or sent to a specific waste handling center that is equipped to dispose of electronic components with minimal environmental impact. The approved methods for disposing of clinical waste and electronic waste, however, are normally not compatible with one another. Thus, in the case of a used wound dressing that includes electronic components, the electronic components may be separated from the clinical waste prior to disposal. After separation, the clinical waste portion and electronic waste portions of the spent wound dressing may be sent to different facilities for disposal. Depending on the configuration of the wound dressing, however, separating the electronics from the remainder of the wound dressing may be messy, impractical, and unsanitary.

The illustrative embodiments include a wound dressing that functions as a single unit to treat a wound but allows for the separation of the electronic components from components that have absorbed clinical waste prior to disposal. Such a wound dressing allows the appropriate disposal of the clinical waste and recycling of electronic components. The illustrative embodiments also include wound dressing components that may be recombined to enable a wound dressing to stay in place while electronic components, such as batteries, are replaced to extend the life of the wound dressing.

The illustrative embodiments provide a reduced-pressure wound dressing having a reliable seal between dressing components that can be broken apart without exposing a user or caregiver to unnecessary contact with fluids absorbed by the dressing. The reduced-pressure wound dressing allows for easy and appropriate disposal of the components depending on the type of waste (e.g., as clinical waste or electronic waste). In addition, the illustrative embodiments provide an integrated wound dressing and reduced-pressure source (i.e., a pump) that may be manufactured either as a single unit or as separate modules. Parts of a modular system may be manufactured in separate facilities and different sterilization processes may be employed to different components of the system. For example, portions of the dressing that include electronic components may be sterilized using Ethylene Oxide, Super Critical Carbon Dioxide, or other sterilization methods that do not degrade the electronics. Other portions of the dressing may be sterilized using other methods, such as Gamma Irradiation or E-Beam sterilization, dependent on material compatibility. An illustrative reduced-pressure dressing alleviates the need for a remote reduced-pressure source or therapy unit that is connected via a tube or conduit, as used by more typical dressings that provide reduced pressure to a tissue site. The illustrative reduced-pressure dressing is a self-contained dressing or therapy unit that can be separated on disposal with minimal user intervention and effort.

In one embodiment, an absorbent, reduced-pressure dressing has an onboard reduced-pressure source, control system, and power source. Referring now to the drawings and initially to FIG. 1, an illustrative embodiment of a system 100 for treating a tissue site 102, e.g., a wound 104 or a cavity, with reduced pressure is presented. The tissue site 102 may be, for example, the wound 104 extending through epidermis 156 and into subcutaneous tissue 158, or any other tissue site. Reduced pressure generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site 102. Unless otherwise indicated, values of pressure stated herein are gauge pressures. The reduced pressure delivered may be constant or varied (patterned or random) and may be delivered continuously or intermittently. Consistent with the use herein, unless otherwise indicated, an increase in reduced pressure or vacuum pressure typically refers to a relative reduction in absolute pressure.

The system 100 includes a reduced-pressure dressing 106 for disposing proximate to the tissue site 102. The reduced-pressure dressing 106 includes absorbent materials and has the ability to deliver reduced pressure to the tissue site 102. The reduced-pressure dressing 106 includes an absorbent pouch 114 fluidly sealed and mechanically connected, or coupled, to an electronics pouch 116 by a removable coupling 118, 318 or a sealing member 154, 354 that pneumatically connects the pouches. As used herein, the word "or" is not mutually exclusive. The electronics pouch 116 and absorbent pouch 114 are joined together such that there is a secure bond between the pouches. The secure bond may be a high-frequency weld around the periphery of the electronics pouch 116. FIGS. 2-9 show similar systems, and variation is shown between figures in order to show some of the potential variations in the illustrative system 100.

The system 100 may be used with various different types of tissue sites 102. The tissue site 102 may be the bodily tissue of any human, animal, or other organism, including bone tissue, adipose tissue, muscle tissue, dermal tissue, vascular tissue, connective tissue, cartilage, tendons, ligaments, body cavity or any other tissue. Treatment of the tissue site 102 may include removal of fluids, e.g., exudate or ascites.

Referring again to FIG. 1, the electronics pouch 116 of the reduced-pressure dressing 106 is formed by coupling a first electronics cover 120 to a second electronics cover 122, wherein the second electronics cover 122 is on the patient-facing side of the electronics pouch 116. In one embodiment, one or more sub parts. e.g., sheets of elastomeric film, form the first electronics cover 120 and the second electronics cover 122. The electronics pouch 116 may also be formed by other techniques such as casting or molding the electronics pouch 116 from a polymer. The electronics pouch 116, or pump pouch, of FIG. 1 includes a pump 108. Within the electronics pouch 116, the pump 108 is mounted to a substrate 132 (532) that is formed from a printed circuit board material such as polyimide, phenolic or another suitable material. The electronics pouch may also include a processor, a power source, and a communication system (not shown) that control the pump 108, power the pump 108, 208, 308, and transmit and receive data. In use, the pump 108 delivers reduced-pressure to the absorbent pouch 114 through an aperture 178, 378 in the substrate 132 that is coupled to the second electronics cover 122. The first electronics cover 120 of the electronics pouch 116 includes a vent 176, 276, 376, 476, 576, 676 to fluidly couple an exhaust from the pump 108 to an exterior of the reduced-pressure dressing 106. An odor filter 177, 277, 377, 577, 777 may be installed within the vent 176 to prevent the reduced-pressure dressing 106 from emitting odor from the wound 104.

The pump 108 may be a micro-pump device and may take numerous forms, such as a piezoelectric pump, peristaltic pump, or other miniaturized pump. In one embodiment, the pump 108 is an acoustic resonance pump that applies the principle of acoustic resonance to generate pressure oscillations within a cavity and motivate fluid through the pump 108. The pump 108 may be the type of micro-pump shown in United States Patent Publication 2009/0240185 (application Ser. No. 12/398,904; filed 5 Mar. 2009), entitled, "Dressing and Method for Applying Reduced Pressure To and Collecting And Storing Fluid from a Tissue Site," which is incorporated herein for all purposes.

The pump 108 is small and light enough to allow the reduced-pressure dressing 106 to be maintained on the tissue site 102 without causing discomfort to the patient. The size and weight of the micro-pump may be such that the reduced-pressure dressing 106 does not pull or otherwise adversely affect the tissue site 102. In one illustrative embodiment, the micro-pump may be a disc pump having a piezoelectric actuator similar to that previously described. Reference is also made to the pumps shown in United States Patent Publication 2009/0087323 and United States Patent Publication 2009/0240185, which are hereby incorporated by reference for all purposes. It should be understood that alternative pump technologies may be utilized and that rotary, linear, or other configurations of pumps may be utilized.

The pump 108 has sufficient flow, reduced pressure, and operation life characteristics to enable continuous application of reduced pressure treatment. The flow may range between about 5-1000 ml/min and the reduced pressure may range between about −50 and −200 mm Hg (−6.6 to −26.6 kPa). It should be understood that alternative ranges may be utilized depending on the configuration of the reduced-pressure dressing 106, size of wound, or type of wound. In one illustrative embodiment, multiple pumps may be positioned in a single dressing to deliver increased flow rates or vacuum levels as required.

In use, the pump 108 generates reduced pressure that is delivered to the tissue site 102 via the absorbent pouch 114. To deliver reduced-pressure to the tissue site 102, the pump 108 applies reduced-pressure through the aperture 178 in the substrate 132 or an aperture in the pump base if no substrate 132 is present. In the embodiment of FIG. 1, a sealing member 154 having a sealing member aperture 140, 240, 440, 540 fluidly couples the electronics pouch 116 to the absorbent pouch 114. The sealing member 154 provides a fluid seal by coupling to, for example, the substrate 132 of the electronics pouch 116 and the absorbent pouch 114. In other embodiments, the reduced-pressure dressing 106 omits the sealing member 154 and the electronics pouch 116 and absorbent pouch 114 are fluidly coupled by a direct coupling. When applying reduced-pressure to the tissue site 102, the absorbent pouch 114 may receive and retain fluids from the tissue site 102.

In one embodiment, the sealing member 154 is a sealing ring that provides a pneumatic seal between the pump 108 and the absorbent pouch 114. One side of the sealing ring may be bonded to the substrate 132 to which the pump 108 is mounted and the other side of the sealing ring may be bonded to the absorbent pouch 114.

The absorbent pouch 114 applies reduced pressure from the pump 108 to the tissue site 102. The absorbent pouch 114 includes a manifold layer 124, 224, 424, 524 formed from a manifold material and is applied adjacent to the tissue site 102 to distribute reduced pressure. Generally, a manifold is a substance or structure that assists in applying reduced pressure to, delivering fluids to, or removing fluids from a tissue site 102. The manifold layer 124 typically includes a plurality of flow channels or pathways that distribute fluids provided to and removed from the tissue site 102 around the manifold layer 124. In one illustrative embodiment, the flow channels or pathways are interconnected to improve distribution of fluids provided to or removed from the tissue site 102. The manifold layer 124 may be a biocompatible material that is capable of being placed in contact with the tissue site 102 and distributing reduced pressure to the tissue site 102. Examples of materials used to form the manifold layer 124 may include without limitation the following: materials that have structural elements arranged to form flow channels, e.g., cellular foam, open-cell foam, porous tissue collections, liquids, gels, and foams that include, or cure to include, flow channels; foam; gauze; felted mat; or any other material suited to a particular biological application.

In one embodiment, the manifold layer 124 is a porous foam and includes a plurality of interconnected cells or pores that act as flow channels. The porous foam may be a polyurethane, open-cell, reticulated foam such as Granu-Foam® material available from Kinetic Concepts, Incorporated of San Antonio, Tex. In some situations, the manifold layer 124 may also be used to distribute fluids such as medications, antibacterials, growth factors, and various solutions to the tissue site 102. Other layers may be included in or on manifold layer 124, such as absorptive materials, wicking materials, hydrophobic materials, and hydrophilic materials.

In one embodiment, the manifold layer 124 distributes reduced pressure generated by the pump 108 and may draw exudate from the wound 104. To retain the exudate, the manifold layer 124 is coupled to an absorbent layer 110, 210, 310 that functions to receive and retain fluids such as exudate from the tissue site 102. The absorbent layer 110 may be made from any material capable of absorbing liquid. For example, the absorbent layer 110 may be made from super absorbent fibers. The super absorbent fibers may retain or bond to the liquid in conjunction with a physical or chemical change to the fibers. In one non-limiting example, the super absorbent fiber may include the Super Absorbent Fiber (SAF) material from Technical Absorbents, Ltd. of Grimsby. United Kingdom. The absorbent layer 110 may be a sheet or mat of fibrous material in which the fibers absorb liquid from the tissue site 102. The structure of the absorbent layer 110 that contains the fibers may be either woven or non-woven. The fibers in the absorbent layer 110 may gel upon contact with the liquid, thereby trapping the liquid. Spaces or voids between the fibers may allow reduced pressure that is applied to the absorbent layer 110 to be transferred within and through the absorbent layer 110.

To prevent liquid (e.g., exudate) from escaping the absorbent pouch 114 and entering the electronics pouch 116, a liquid-air separator 112, 212, 412, 512, e.g., a hydrophobic filter, may be placed between absorbent layer 110 and a first cover of the absorbent pouch 114. In such an embodiment, the first cover 126 of the absorbent pouch 114 is coupled about the perimeter of the sealing member 154 to form a fluid seal.

In an embodiment, an intermediate manifold may be applied between the reduced-pressure dressing 106 and a portion of the tissue site 102. The intermediate manifold may be constructed from bioresorbable materials that may remain in a patient's body following use of the reduced-pressure dressing 106. Suitable bioresorbable materials may include, without limitation, a polymeric blend of polylactic acid (PLA) and polyglycolic acid (PGA). The polymeric blend may also include without limitation polycarbonates, polyfumarates, and capralactones. The intermediate manifold may further serve as a scaffold for new cell-growth, or a scaffold material may be used in conjunction with the intermediate manifold to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials. In an embodiment, the reduced-pressure dressing 106 also includes an interface layer, or comfort layer, for placing between the tissue site 102 and the manifold layer 124.

The absorbent pouch 114 maintains a fluid coupling with the tissue site 102 to apply reduced-pressure. As such, the perimeter of the absorbent pouch 114 may be coupled to the tissue site 102 to form a sealed space. This coupling creates a fluid seal around the tissue site 102 that may be achieved by coupling the first cover 126 of the absorbent pouch 114 to the tissue site 102 using an attachment device. In such an embodiment, the first cover 126 is coupled to the manifold layer 124 or a comfort layer so that the absorbent layer 110 will maintain structural integrity when removed from the tissue site 102. In another embodiment, the first cover 126 is coupled to a second cover 128 in the manner described above with regard to the first electronics cover 120 and second electronics cover 122 of the electronics pouch 116. In an embodiment, the second cover 128 is coupled to the tissue site 102 to create the fluid seal when the reduced-pressure dressing 106 is applied to the tissue site 102. Upon removal of the reduced-pressure dressing 106 from the tissue site 102, the coupling between the first cover 126 and second cover 128 prevents the layers of the absorbent pouch 114 from separating so that the absorbent pouch 114 may be discarded as a unit.

To maintain the fluid seal, the first cover 126 and second cover 128 of the absorbent pouch 114, and the first electronics cover 120 and second electronics cover 122 of the electronics pouch 116 may be formed from an impermeable or semi-permeable, elastomeric material. Elastomeric materials have the properties of an elastomer or, more generally, a polymeric material that has rubber-like properties. More specifically, most elastomers have ultimate elongations greater than 100% and a significant amount of resilience. The resilience of a material refers to the material's ability to recover from an elastic deformation. Examples of elastomers include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of dressing sealing member materials include a silicone drape, 3M Tegaderm® drape, polyurethane (PU) drape such as one available from Avery Dennison Corporation of Pasadena, Calif. The reduced-pressure dressing forms a sealed space over the tissue site 102, which may or may not contain the pump 108. The elastomeric material may be a tin, flexible elastomeric film.

An attachment device 162 may be used to couple the first cover 126 or second cover 128 to the patient's epidermis or another intermediate layer, such as a gasket or additional sealing device. The attachment device 162 may take numerous forms. For example, the attachment device 162 may be a medically acceptable, pressure-sensitive adhesive that extends about a periphery or all of the first cover 126 (or second cover 128) or covers at least a portion of a patient-facing side of the reduced-pressure dressing 106 over the epidermis 156.

As noted above, the reduced-pressure dressing 106 includes the removable coupling 118 between the electronics pouch 116 and the absorbent pouch 114. The removable coupling 118 allows a caregiver to separate the electronics pouch 116 from the absorbent pouch 114 by exerting a force on a portion of the electronics pouch 116, such as tab 130, 430, 530, 730. An example of such a removable coupling is described in more detail with regard to FIGS. 2-4.

Turning now to FIGS. 2-4, the reduced-pressure dressing 206 includes a removable coupling 218 that facilitates the separation of the electronics pouch 216 from the absorbent pouch 214 after use. The removable coupling 218 includes a first bond 236 and a second bond 238, 438, 538 offset from the first bond 236. The first bond 236 and second bond 238 may be any suitable type of joining technology, bond or coupling, including a high frequency weld, an ultrasonic weld, a heat weld, an adhesive bond, and a molded part line. In one embodiment, the first bond 236 couples a second electronics cover 222 to a first cover 226 of an absorbent pouch 214. The second bond 238 is offset from the first bond 236 and further from the perimeter 278 of the reduced-pressure dressing 206 than the first bond 236. The first bond 236 should be strong enough so that unintended separation of the electronics pouch 216 from the absorbent pouch 214 does not occur. The first bond 236 may be a weld or other joint that provides a pneumatic seal, but a pneumatic seal between the pouches may instead be provided by another component or weld that is within the boundary of the first bond 236, such as a sealing member 254. A perforation 234 extends through the first electronics cover 220 and second electronics cover 222 between the first bond 236 and second bond 238, i.e., inside of the first bond 236 but outside of the second bond 238. The perforation 234 provides a separation line where the first electronics cover 220 and second electronics cover 222 can be torn to separate the electronics pouch 216 from the absorbent pouch 214. To facilitate separation of the electronics pouch 216 from the absorbent pouch 214, the first electronics cover 220 may include a tab 230 bonded to the first electronics cover 220 using any of the bond types described above, or formed integrally to the first electronics cover 220. Alternatively, the first electronics cover 220 may include a hole that allows a separation force to be exerted on the electronics pouch 216. In one embodiment, pulling the tab 230 causes a tear to develop and propagate along the weakened path of the perforation 234 until the electronics pouch 216 separates from the absorbent pouch 214.

In one embodiment, the first bond 236 couples the second electronics cover 222 to both the first electronics cover 220 and first cover 226. In another embodiment, the first bond 236 couples the first electronics cover 220 to the second electronics cover 222. In such embodiments, the second electronics cover 222 couples to the first cover 226 at any suitable location that is outside of the perforation 234 to preserve the coupling of the electronics pouch 216 to the absorbent pouch 214 until the electronics pouch 216 is torn along the perforation 234.

The dimensions of the perforation 234 are dependent on the material used to manufacture the electronics pouch 216 or absorbent pouch 214 as well as the location of the perforation 234. The perforation 234 should weaken the material so that the strength of the perforated area is significantly less than the tear strength of the pouch material. In an embodiment where the material is Exopack DEV 09-80A or Inspire 70980, the perforation 234 may have the dimensions of 0.1 mm land and between 0.1 mm and 0.5 mm space.

FIG. 3 illustrates a possible arrangement of the first bond 236, perforation 234, and second bond 238 and FIG. 4 shows how the electronics pouch 216 separates from the absorbent pouch 214 after being torn along the perforation 234. When separated, the portion of the reduced-pressure dressing 206 that retains the absorbent pouch 214 has a first perforation line 234a and the electronics pouch 216 has a second perforation line 234b indicating the points of separation. In the illustrative embodiment of FIGS. 2-4, the sealing member 254 is shown as being coupled to the patient-facing side of the electronics pouch 216 and releasably coupled to the absorbent pouch 214. In another embodiment, however, the sealing member 254 is coupled to the absorbent pouch 214 and releasably coupled to the electronics pouch 216.

In an embodiment, the sealing member 254 is a sealing ring, and an adhesive is used to couple the sealing ring to the substrate 232 of the pump 208 or to the first cover 226 of the absorbent pouch 214. The properties of the adhesive applied to the surfaces of the sealing ring may be altered so that when the pouches are separated, the sealing ring remains adhered to either the substrate 232 or the first cover 226. If the sealing ring is attached by welding, the seal ring itself can have a weakened area to facilitate tearing to separate the sealing ring from the electronics pouch 216 or absorbent pouch 214 when the electronics pouch 216 is removed. The sealing ring may then be disposed appropriately. Adhesives that may be used to adhere the sealing ring to the substrate 232 of the first cover 226 Acrylic Pressure Sensitive Adhesives (PSA) based such as 3M 927, or a UV liquid adhesive such as Dymax 1201-M-SC.

The sealing member 254 may be a single flexible material that has adhesive coating on each side to couple to the electronics pouch 216 and absorbent pouch 214. The sealing member 254 also provides a fluid seal between the electronics pouch 216 and absorbent pouch 214. The flexible material may be a closed cell foam, such as a foam manufactured from neoprene or ethylene-vinyl acetate (EVA). Additionally, the flexible material may provide a level of padding between the electronics pouch 216 and absorbent pouch 214, thereby adding flexibility to the reduced-pressure dressing 206. In an embodiment, the sealing member material may be a solid elastomeric material, such as a thermoplastic elastomer (TPE), or a rigid material. Where an adhesive is used to hold the sealing member 254 in place, the adhesive properties can be altered between the two sides of the sealing member 254 so that on separation, the sealing member 254 remains coupled to either the electronics pouch 216 or the absorbent pouch 214.

In another embodiment, the electronics pouch 216 couples directly to the absorbent pouch 214. In such an embodiment, a portion of the electronics pouch 216 or the absorbent pouch 214 may include a breakaway feature, such as a weakened area in the pouch material or a breakaway feature in the substrate 232 to facilitate separation of the pouches.

Together, FIGS. 2-4 show that a caregiver may separate the electronics pouch 216 from the absorbent pouch 214 by grasping the tab 230 and exerting a force to tear the first electronics cover 220 and second electronics cover 222 around the perimeter of the electronics pouch 216. After generating the tear, the electronics pouch 216 may be grasped and pulled to apply pressure to the sealing member 254, which may be a sealing ring. Once the sealing member 254 is separated from the electronics pouch 216, the electronics pouch 216 is completely free from the absorbent pouch 214 and the pouches may be discarded separately.

FIG. 5 shows another illustrative embodiment of a reduced-pressure dressing 306 that is similar in many respects to the dressings of FIGS. 1-4 but omits a second electronics cover. In the embodiment, an upper layer of the absorbent pouch 314, such as the a liquid-air separator 312, is coupled to the first cover 326 by a first bond 336. Inside of the first bond, the first cover 326 includes a perforation 334. Inside of the perforation 334, the first cover 326 is coupled to the first electronics cover 320 by a second bond 338. In this embodiment, the first cover 326 is also coupled to the substrate 332 that forms a portion of patient-facing side of the electronics pouch 316. Similar to the embodiments of FIGS. 1-4, the reduced-pressure dressing 306 may be torn along the perforation 334 to separate the electronics pouch 316 from the absorbent pouch 314. In this embodiment, the tab 330 may merely be an extension of the first electronics cover 320.

Figure 6A:
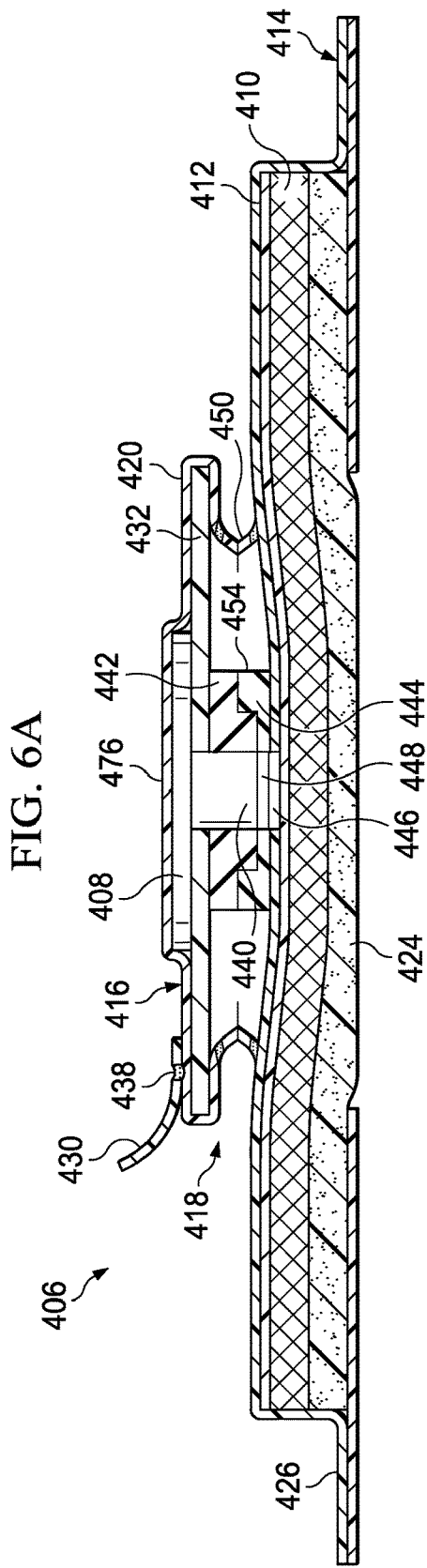
FIG. 6A is a side, cross-section view of an illustrative embodiment of a reduced-pressure dressing having an intermediate cover member and a sealing member that comprises a first sealing member connector and a second sealing member connector.
Figure 6B:
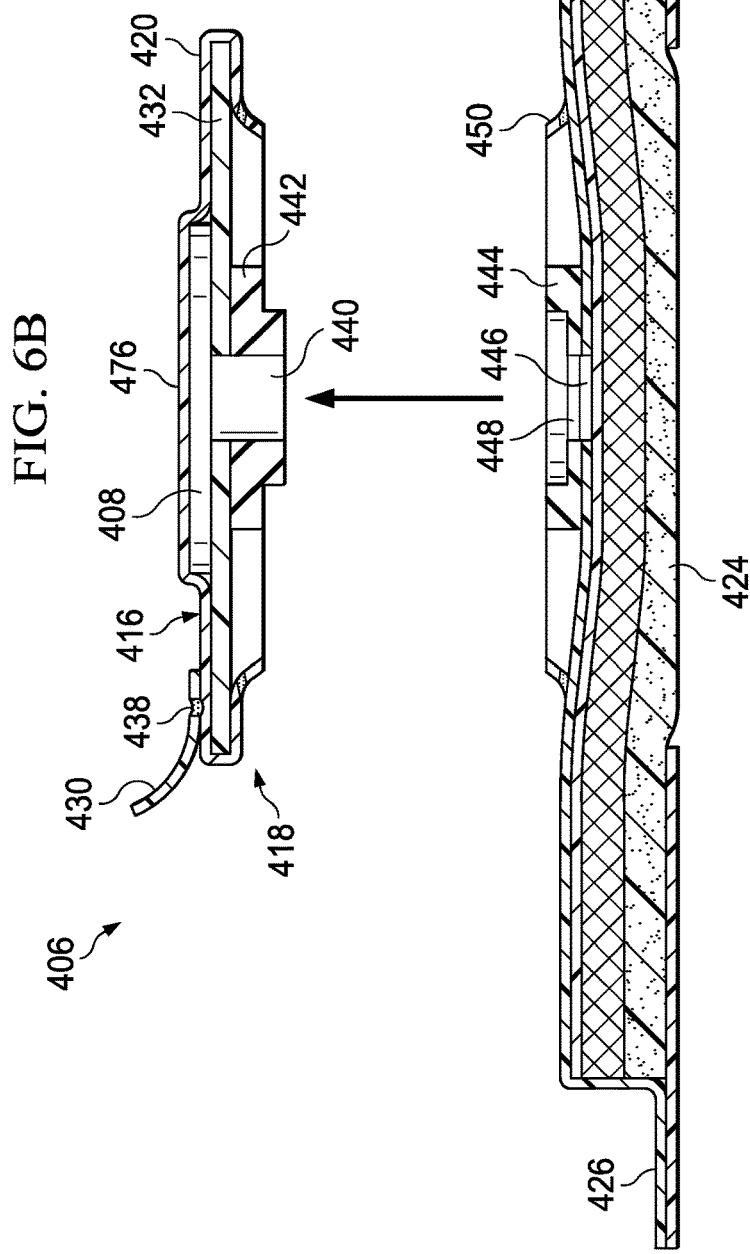
FIG. 6B is a detail, cross-section view of the reduced-pressure dressing of FIG. 6 in an exploded state.

FIGS. 6A and 6B show another illustrative embodiment of a reduced-pressure dressing 406 having an electronics pouch 416 attached to an absorbent pouch 414 by a removable coupling 418. In the embodiment, the first cover 426 of the absorbent pouch 414 is coupled to a proximate side of the sealing member 454. The opposing side of the sealing member 454 is coupled to the second electronics cover 422 or the substrate 432 of the electronics pouch 416. In addition, the first cover 426 and first electronics cover 420 (or second electronics cover 422) are coupled to one another by the removable coupling 418, which is an intermediate cover member 450. The intermediate cover member 450 may include a perforation or be formed of a material that is easier to tear than the material that forms the pouches to facilitate separation of the electronics pouch 416 from the absorbent pouch 414.

In an embodiment, the intermediate cover member 450 provides a fluid seal between the electronics pouch 416 and the absorbent pouch 414, thereby alleviating the need for a sealing member 454. The intermediate cover member 450 may add flexibility between the absorbent pouch 414 and electronics pouch 416 in such an embodiment. The intermediate cover member 450 is bonded to the substrate 432 to which the pump 408 is mounted and bonded or welded to the first cover 426 of the absorbent pouch 414. The material that forms the intermediate cover member 450 is selected such that, when the electronics pouch 416 is separated from the absorbent pouch 414, the intermediate cover member 450 will break before the integrity of either pouch is compromised. In another embodiment, the separation occurs at either the bond between the intermediate cover member 450 and the absorbent pouch 414 or the bond between the intermediate cover member 450 and the electronics pouch 416.

In one embodiment, the sealing member 454 is formed from a first sealing connector 442 coupled to the substrate 432 of the electronics pouch 416 and a second sealing connector 444 coupled to the absorbent pouch 414. The first sealing connector 442 is releasably coupled to the second sealing connector 444. As FIG. 6B shows, the releasable coupling between the first sealing connector 442 and second sealing connector 444 results in the first sealing connector 442 remaining coupled to the electronics pouch 416 and the second sealing connector 444 remaining coupled to the absorbent pouch 414 when the pouches are separated. In one embodiment the sealing member 454 or second sealing connector 444 includes additional elements, such as a liquid-air separator 446 and an odor filter 448. Including the liquid-air separator 446 within the sealing member 454 may alleviate the need for such an element in the absorbent pouch, enabling a smaller part to perform the function of preventing liquids (e.g., exudate) from entering the electronics pouch 416. Similarly, the sealing member 454 may include the odor filter 448, which may be a charcoal filter, thereby alleviating the need to install such an element in another portion of the reduced-pressure dressing 406. The sealing member 454 may be formed from a polymer, such as a polyvinyl chloride (PVC) or acrylonitrile butadiene styrene (ABS) polymer. In an embodiment, the sealing member 454 may instead be formed from polyurethane or another suitable material that is compatible with the pouch cover material and weldable using a high-frequency welding process. In one embodiment, the sealing member 454 couples to the second electronics cover 422 or directly to the substrate 432 using an adhesive.

In one embodiment, a breakable connection piece is securely bonded to both the electronics pouch 416 and absorbent pouch 414 to serve the function of both a sealing member 454 and intermediate cover member 450. In such an embodiment, the pouches may be separated by breaking the breakable connection piece. Such a breakable connection piece may be manufactured from a plastic molding having a weakened breakaway area that causes the breakable connection piece to break in a predictable and controllable manner. The breakable connection piece may be made from an injection molded thermoplastic polyurethane (TPU), such as Pellethane® 2363-80AE having a durometer of 80 on the Shore A scale. The thickness of the weakened area may be in the range of 0.05 mm to 0.08 mm, thereby enabling a controlled tear, or break, to be induced without risking damage or undesirable disassembly of the electronics pouch 416 or absorbent pouch 414. In an embodiment, the breakable connection piece contains an odor filter and a liquid-air separator. The breakable connection piece may also be manufactured from a porous polymer, e.g., a sintered polymer, that has been treated to provide liquid and odor blocking functions. For example, the breakable connection piece may include hydrophobic materials for liquid separation and activated carbon particles for odor control. In the case of a sintered polymer material, the breakable connection piece would not include an aperture, but would be a gas permeable structure having a sealed outer surface such that gas would be pulled through the breakable connection piece to transmit reduced-pressure. In such an embodiment, the outer surface of the breakable connection piece formed from the sintered polymer should be coated with a gas impermeable coating to provide a seal.

Where the intermediate cover member 450 is a breakable connection piece having a breakaway feature, the breakable connection piece may include an electrical connection. The electrical connection may electrically couple one or more sensors in the absorbent layer 410 to the processor of the electronics pouch 416. In such an embodiment, the reduced-pressure dressing 406 may include sensors to measure the fluid capacity of the dressing, the mechanical or pneumatic pressure at the tissue site, the pH of the wound, and other characteristics of the tissue site. The electrical coupling may also be used to provide power to a therapeutic system mounted within the absorbent layer 410 that requires power or monitoring, such as a wound camera or electrical stimulation system. In such an embodiment, a RF device, such as a RFID antenna, may be mounted in the reduced-pressure dressing 406 and the breakable connection piece may provide additional space to mount related electrical components. In addition, the breakable connection piece may provide multiple channels or lumens from the electronics pouch 416 to the absorbent pouch 414, which may enable the monitoring of pressure in specific areas of the reduced-pressure dressing. In such an embodiment, a TRAC system may be used to determine absorbent saturation or other characteristics of a tissue site where substances are being delivered to a wound. In such an embodiment, the reduced-pressure dressing may be configured to deliver anti-microbial agents, analgesics, and cleansing solutions.

In another embodiment, the intermediate cover member 450 is an adhesive layer that provides a fluid seal between the electronics pouch 416 and absorbent pouch 414. The adhesive layer may be configured to allow the electronics pouch 416 to be separated from the absorbent pouch 414 by peeling the pouches apart.

Alternatively, the intermediate cover member 450 may be a film joined to the electronics pouch 416 and absorbent pouch 414 by a suitable method, such as bonding or welding. The film may be manufactured so that the film is weaker than the adjacent materials, thereby allowing the film to break instead of the adjacent electronics pouch 416 and absorbent pouch 414 as the pouches are pulled apart. Alternatively, a separation mechanism such as a string or strip of material is included beneath the film, such that pulling the string outward will cause the string or strip to unwind and tear the film to facilitate separation of the pouches.

Figure 7:
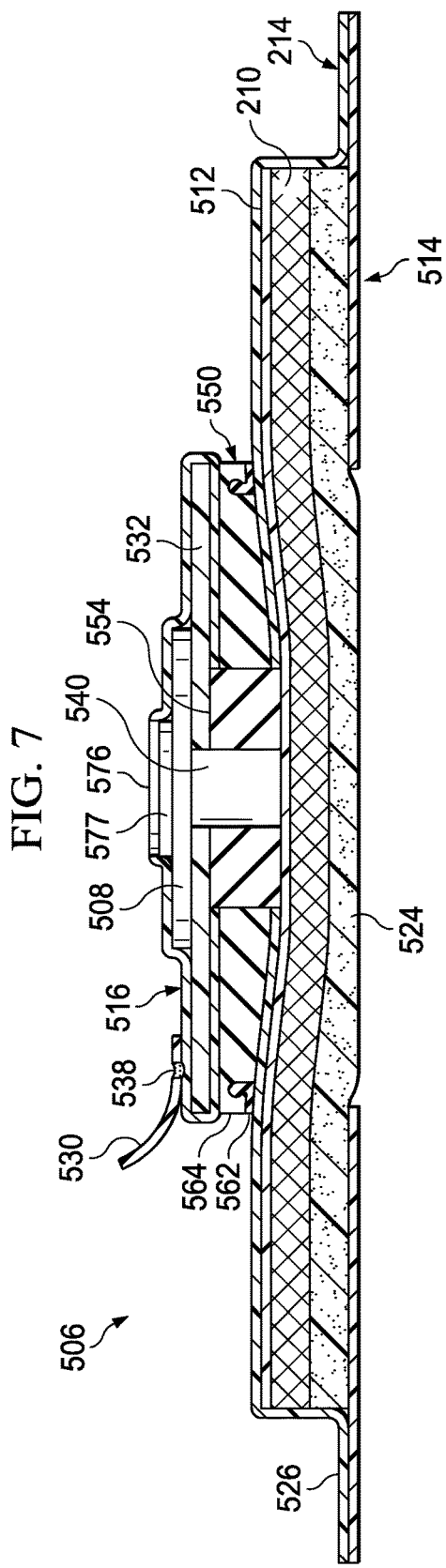
FIG. 7 is a side, cross-section view of an illustrative reduced-pressure dressing having an intermediate cover member that comprises a first cover connector and a second cover connector.

FIG. 7 shows another illustrative embodiment of a reduced-pressure dressing 506 that includes an electronics pouch 516 and an absorbent pouch 514. In the embodiment, reduced-pressure is transmitted from a pump 508 of the electronics pouch 516 to the absorbent pouch 514 via sealing member 554. The electronics pouch 516 is coupled to the absorbent pouch 514 by an intermediate cover member 550 that is manufactured from multiple parts, such as a first cover connector 562 and a second cover connector 564. The first cover connector 562 and second cover connector 564 are formed from different polymers so that adhesion between the first cover connector 562 and second cover connector 564 is strong enough to provide a fluid seal but weak enough to be easily broken. For example, if the first cover connector 562 is fabricated from polyurethane, then the second cover connector may be formed from polypropylene or high-impact polystyrene. In addition, the second cover connector 564 may be formed from polyurethane or another suitable material that is compatible with the pouch cover material and weldable using a HF welding process. In an embodiment, a fluid seal between the first cover connector 562 and second cover connector 564 is obtained by an interference fit between the connectors. As such, the first cover connector 562 and second cover connector 546 may be mating parts having a snap fit or twist-lock feature with sealing surfaces to maintain a fluid seal. The first cover connector 562 is coupled to the first cover 526 of the absorbent pouch 514 by an adhesive or weld, or by forming the first cover connector integrally to the first cover 526. The second cover connector 564 couples to the electronics pouch 516 in a similar manner.

In an embodiment having the first cover connector 562 and second cover connector 564, one of the parts, e.g., the first cover connector 562 may be manufactured by injection molding. The second cover connector 564 is then combined with the first cover connector 562 using an overmolding process. The overmolding process allows different materials to be used that are optimized for the joining process used at each interface. For example, the first cover connector 562 may be suitable for welding to a polymer surface of the absorbent pouch 514 while the second cover connector 564 is better suited for adhesive bonding to a surface of the electronics pouch 516 (e.g., to a polyimide or phenolic PCB substrate).

To form the second cover connector 564, the first cover connector 562 is installed in a mold, which is used to form the second cover connector 564 by overmolding the second cover connector 564 to the first cover connector 562. The overmolding process results in a part line 566 at the junction of the first cover connector 562 and second cover connector 564. The part line 566 may be formed such that when a separation force is applied to the pouches, the electronics pouch 516 separates from the absorbent pouch 514 along the part line 566. The part line 566 may be a flat surface or may include a mechanical interlock feature that enhances sealing. Where the fluid seal is enhanced by an interlock feature, the polymeric bond between the first cover connector 562 and second cover connector 564 is less important for the purposes of creating a fluid seal, and a weaker bond may be acceptable. As such, the first cover connector 562 and the second cover connector 564 may be formed from dissimilar materials that will not form a strong bond to one another. Also, a coating may be applied to the first cover connector 562 along the part line 566 to prevent the second cover connector 564 from permanently bonding to the first cover connector 562. In this way, the first cover connector 562 may be removably coupled to the second cover connector 564 to maintain a fluid seal until the electronics pouch 516 is separated from the absorbent pouch 514.

A fluid seal between the first cover connector 562 and second cover connector 564 may be more easily obtained by using an overmolding process than another manufacturing process because manufacturing tolerances and dimensional variations at the interface are negated by the overmolding process. The overmolding process also facilitates the joining of dissimilar materials. For example, in an embodiment in which there is a difference in hardness between the first cover connector 562 and the second cover connector 564, the connector formed from the softer polymer is formed using the overmolding process, while the opposing connector is formed using the injection molding process.

The use of dissimilar materials may also facilitate separation. Where the first cover connector 562 and second cover connector 564 include mechanical interlocking features, the softer connector may be more easily deformed to separate from the harder connector. In another embodiment both the first cover connector 562 and second cover connector 564 are injection molded and assembled together to provide a sealed coupling. In embodiments in which a more rigid part is manufactured from a material other than a thermoplastic (e.g., thermoset polymer), other manufacturing techniques may be employed.

In an embodiment, the absorbent pouch 514 remains in place at a tissue site while the electronics pouch 516 is removed to, for example, renew the power source of the pump 508. The power source of the pump 508 may be replaced within the electronics pouch 516 and the electronics pouch 516 may be reapplied or replaced with a new electronics pouch 516 to extend the life of the reduced-pressure dressing 506.

Figure 8A:
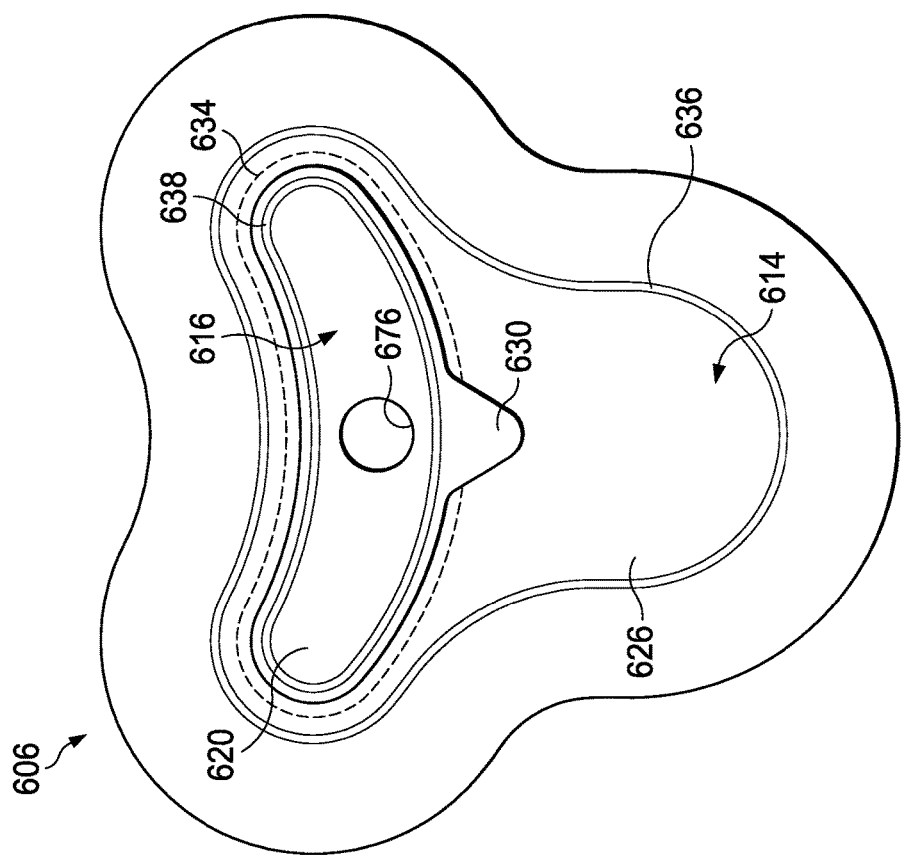
FIG. 8A is a top view of an illustrative embodiment of a reduced-pressure dressing having an arcuate shape.

FIGS. 8A and 8B show an embodiment of a reduced-pressured dressing 606 having an arcuate shape. Aside from the arcuate shape, the reduced-pressure dressing 606 is generally analogous to the dressing of FIG. 1. For example, the reduced-pressure dressing 606 includes an absorbent pouch 614 having a first cover 626. The absorbent pouch 614 receives reduced-pressure from a pump that is housed within an electronics pouch 616. The electronics pouch 616 is removably coupled to absorbent pouch at a first bond 636 and a second bond 638. Adjacent the second bond 638, the reduced-pressure dressing 606 includes a perforation 634 that facilitates the separation of the absorbent pouch 614 from the electronics pouch 616. The first cover 620 of the electronics pouch 616 includes a tab 630 that can be pulled to initiate a tear along the perforation 634 to separate the pouches.

Figure 9:
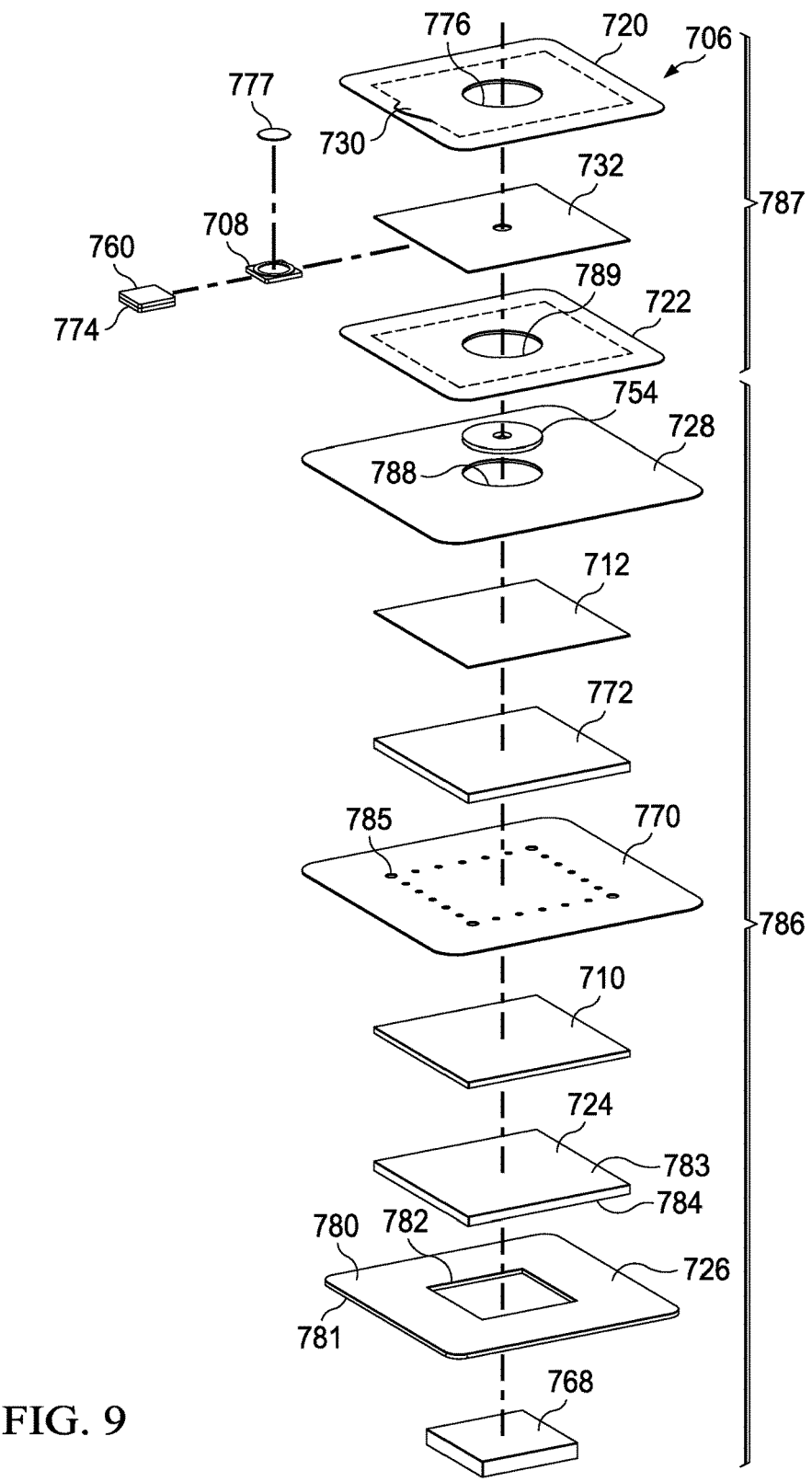
FIG. 9 is an exploded, perspective view of an illustrative embodiment of a reduced pressure dressing having first envelope that is removably coupled to a second envelope.

FIG. 9 shows an exploded view of a reduced-pressure dressing 706 that contains additional layers but is similar in many respects to the dressings discussed above. The reduced-pressure dressing 706 is shown in a rectangular form but may be formed to have any suitable shape for application to a tissue site. For example, the reduced-pressure dressing may be shaped to resemble the reduced-pressure dressing 606 of FIGS. 8A and 8B.

The reduced-pressure dressing 706 includes an optional intermediate manifold 768 that may be placed adjacent the tissue site, as discussed above. The reduced-pressure dressing 706 includes a first cover 726 and a second cover 728. The second cover 728 has a first side 780 and a second, patient-facing side 781. The second, patient-facing side 781 may be coated with a releasable adhesive to facilitate application to a tissue site. The second cover 728 also includes a treatment aperture 782 for placing over a portion of the tissue site (e.g., a wound) that receives reduced pressure. The reduced-pressure dressing 706 also includes a manifold layer 724, which is an internal distribution manifold having a first side 783 and a second, patient-facing side 784. In use, the manifold layer 724 distributes reduced-pressure to the tissue site. The second, patient-facing side 784 of the manifold layer 724 is coupled to the first side 780 of the second cover 728. An absorbent layer 710, which functions to receive and retain fluids from a tissue site, is coupled to the manifold layer 724.

A diverter layer 770 is coupled to the absorbent layer 710. The diverter layer 770 is disposed adjacent to the absorbent layer 710 and the manifold layer 724. The diverter layer 770 is formed from a liquid impermeable material but contains a plurality of apertures 785. The plurality of apertures 785 allow reduced pressure to be transmitted through the diverter layer 770 at desired locations. The diverter layer 770 helps control the pattern of reduced pressure as applied to the absorbent layer 710. The reduced pressure is distributed to the diverter layer 770 by a second manifold layer 772 that is coupled to the diverter layer 770. The apertures 785 may be arranged in a pattern for applying the reduced pressure to portions of the absorbent layer 710 to enhance the capability of the absorbent layer 710 to continue transferring reduced pressure to the tissue site as the absorbent layer 710 absorbs more fluid from the tissue site. The diverter layer 770 acts in conjunction with the second manifold layer 772 to ensure that the absorption capabilities and absorption efficiency of the absorbent layer 710 are increased relative to an absorbent layer 710 that is not used in conjunction with a diverter layer 770. By providing better distribution of liquid throughout the absorbent layer 710, the diverter layer 770 also increases the effective capacity and treatment time of the reduced-pressure dressing 706.

The diverter layer 770 may be made from any material that enhances the reduced pressure transmission and storage capabilities of an adjacent absorbent layer. For example, the diverter layer 770 may be made from a material that is substantially impermeable to liquid and gas and that diverts the reduced pressure to pass through apertures 785. Alternatively or in addition, the material from which the diverter layer 770 is made may have a predetermined moisture vapor transfer rate that is consistent with gas permeability. In either example, the diverter layer 770 may still include a pattern of apertures for transmitting a greater volume of liquid or gas than that permitted by a gas-permeable material not having apertures. It should be noted, however, that permeability of the diverter layer 770 to gas but not liquid may result in increased transmission of reduced pressure through the dressing while still directing liquid flow around or near the perimeter of the diverter layer 770.

In this embodiment, the reduced-pressure dressing 706 includes a liquid-air separator 712 coupled to the second manifold layer 772 and the first cover 726, which is coupled about the perimeter to the second cover 728. The first cover 726 includes an aperture 788 to receive reduced pressure. Together, the first cover 726 and second cover 728 form a first envelope 786 enclosing the manifold layer 724, absorbent layer 710, diverter layer 770, second manifold layer 772, and liquid-air separator 712.

To generate reduced pressure, the reduced-pressure dressing 706 includes a pump 708. The pump is mounted to a substrate 732 and coupled to a processor 760 and a power source 774. Additional electronic components may be coupled to the pump 708, processor 760, or power source 774 as desired. The substrate 732 is enclosed between a first electronics cover 720, which is coupled to a second electronics cover 722 to form a second envelope 787. The first electronics cover 722 also includes a vent 776 to fluidly couple an exhaust of the pump 708 to the external environment and an odor filter may be installed between the exhaust of the pump 708 and the vent 776 to prevent odor from a wound from escaping the reduced-pressure dressing 706. The substrate 732 and second electronics cover 722 also include an aperture 789 to facilitate the transmission of reduced pressure to the first envelope 786.

The second envelope 787 is removably coupled to the first envelope 786 using a removable coupling that provides a fluid seal. For example, a portion of the second electronics cover 722 may be coupled to a portion of the second cover 728. Optionally, a sealing member 754 provides a sealed fluid path between the second envelope 787 and the first envelope 786. The sealing member 754 includes an aperture for transmitting reduced-pressure generated by the pump 708 to the layers of the first envelope 786 for application to the tissue site.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

I claim:

1. A reduced-pressure dressing for applying reduced pressure treatment to a tissue site, the reduced-pressure dressing comprising:
    an absorbent pouch comprising:
        a manifold layer adapted to deliver reduced pressure to the tissue site,
        an absorbent layer in fluid communication with the manifold layer to absorb liquid from at least one of the manifold layer and the tissue site, and
        a first cover positioned over the absorbent layer and the manifold layer to maintain the reduced pressure at the tissue site; and
    an electronics pouch coupled to the absorbent pouch by a first bond, the electronics pouch comprising:
        a second cover having a first electronics cover and a second electronics cover, the second electronics cover coupled to the first electronics cover by a second bond offset from the first bond, the electronics pouch removably coupled from the absorbent pouch with a perforation located between the first bond and the second bond, and a pump adapted to provide fluid communication to the tissue site through at least one of the absorbent layer and the manifold layer, wherein the pump is positioned between the first electronics cover and the second electronics cover.

2. The reduced-pressure dressing of claim 1, wherein:
the second cover comprises a tab, and
the perforation is operable to tear in response to an application of a separating force to the tab, thereby separating the electronics pouch from the absorbent pouch.

3. The reduced-pressure dressing of claim 2, wherein the perforation is of 0.1 mm length and 0.5 mm width.

4. The reduced-pressure dressing of claim 1, wherein:
the electronics pouch comprises a circuit board;
the pump is mounted to the circuit board;
the reduced-pressure dressing comprises a sealing member coupled to the circuit board and the absorbent pouch; and
the sealing member provides a fluid seal between the pump and the absorbent pouch.

5. The reduced-pressure dressing of claim 4, wherein the sealing member comprises a liquid-air separator.

6. The reduced-pressure dressing of claim 4, wherein the sealing member comprises an odor filter.

7. The reduced-pressure dressing of claim 4, wherein the sealing member comprises liquid-air separator and a carbon filter.

8. The reduced-pressure dressing of claim 4, wherein the sealing member comprises a sealing ring.

9. The reduced-pressure dressing of claim 4, wherein the sealing member comprises a closed celled foam.

10. The reduced-pressure dressing of claim 4, wherein the sealing member comprises neoprene.

11. The reduced-pressure dressing of claim 4, wherein the sealing member comprises a first sealing connector and a second sealing connector.

12. The reduced-pressure dressing of claim 1, wherein the second cover is bonded to the first cover by a first cover connector and a second cover connector.

13. The reduced-pressure dressing of claim 12, wherein the first cover connector and second cover connector comprise polyurethane.

14. The reduced-pressure dressing of claim 1, wherein:
the second cover is coupled to the first cover by an intermediate cover member;
the intermediate cover member is more susceptible to tearing than the first cover and the second cover; and
the electronics pouch and absorbent pouch are separable by tearing the intermediate cover member.

15. The reduced-pressure dressing of claim 1, further comprising a sealing layer positioned between the first cover and tissue at or near the tissue site.

16. The reduced-pressure dressing of claim 1, wherein the pump is a piezoelectric-driven micropump.

17. The reduced-pressure dressing of claim 1, wherein the electronics pouch further comprises a battery and control electronics positioned within the electronics pouch and operatively connected to the pump.

18. The reduced-pressure dressing of claim 1 further comprising an aperture in the second cover to allow exhausting of gas from the pump.

19. The reduced-pressure dressing of claim 1 further comprising an odor filter in fluid communication with an outlet port of the pump.

20. The reduced-pressure dressing of claim 1, wherein the absorbent pouch further comprises:
a liquid-air separator to inhibit liquid from exiting the absorbent pouch; and
a diverter layer between the liquid-air separator and the absorbent layer, the diverter layer including a plurality of apertures to transmit reduced pressure from the pump to the absorbent layer.

21. The reduced-pressure dressing of claim 20, wherein:
a surface area of the diverter layer is greater than a surface area of the first cover; and
at least a portion of the first cover is adhesively coupled to the diverter layer and at least a portion of the diverter layer is coupled to a tissue surrounding the tissue site.

22. The reduced-pressure dressing of claim 20 further comprising a seal layer positioned between the diverter layer and tissue surrounding the tissue site.

23. The reduced-pressure dressing of claim 1, wherein the manifold layer is hydrophobic.

24. The reduced-pressure dressing of claim 1, wherein the absorbent layer includes a super-absorbent fiber.

25. The reduced-pressure dressing of claim 1, wherein the absorbent pouch further comprises:
a first manifold layer in fluid communication with the manifold layer;
a diverter layer formed from a gas-impermeable material, the diverter layer including a plurality of spaced apertures in fluid communication with the absorbent layer;
a second manifold layer in fluid communication with the diverter layer;
a liquid-air separator positioned between the second manifold layer and the pump to inhibit liquid from entering the pump,
wherein the absorbent layer is in fluid communication with the first manifold layer to absorb liquid from at least one of the first manifold layer, the manifold layer, and the tissue site; and
wherein the pump is in fluid communication with the second manifold layer to deliver a reduced pressure to the tissue site.

* * * * *